(12) United States Patent
Fung et al.

(10) Patent No.: US 11,944,536 B2
(45) Date of Patent: Apr. 2, 2024

(54) TRANSCATHETER SELF-EXPANDABLE TRICUSPID VALVE REPLACEMENT SYSTEM

(71) Applicant: The Chinese University of Hong Kong, Hong Kong (CN)

(72) Inventors: Erik Yee Mun George Fung, Hong Kong (CN); Tze Chuen Ng, Hong Kong (CN); Philip Wai Yan Chiu, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 0 days.

(21) Appl. No.: 16/990,895

(22) Filed: Aug. 11, 2020

(65) Prior Publication Data

US 2021/0045869 A1  Feb. 18, 2021

Related U.S. Application Data

(60) Provisional application No. 62/886,245, filed on Aug. 13, 2019.

(51) Int. Cl.
 *A61F 2/24* (2006.01)
 *A61F 2/82* (2013.01)
 *A61F 2/915* (2013.01)

(52) U.S. Cl.
 CPC ............ *A61F 2/2418* (2013.01); *A61F 2/243* (2013.01); *A61F 2210/0014* (2013.01); *A61F 2220/0075* (2013.01); *A61F 2230/0065* (2013.01)

(58) Field of Classification Search
 None
 See application file for complete search history.

(56) References Cited

U.S. PATENT DOCUMENTS 7,291,168 B2 * 11/2007 Macoviak ............. A61F 2/2412
 623/2.36
7,527,646 B2 * 5/2009 Rahdert ................ A61F 2/2454
 623/2.36

(Continued)

FOREIGN PATENT DOCUMENTS

EP   2478868 A1   7/2012
WO  2014/181336 A1  11/2014

(Continued)

OTHER PUBLICATIONS

Extended European Search Report from European patent application No. 20190688.0, dated Dec. 21, 2020, 7 pages.

*Primary Examiner* — Ann Schillinger
(74) *Attorney, Agent, or Firm* — Kilpatrick Townsend & Stockton LLP (57) ABSTRACT

A tricuspid valve apparatus may include a frame and an associated neo-prosthetic valve. The frame acts as a stabilizing structure that extends cephalad into the morphologic or functional right atrium (upstream) and caudally into the morphologic or functional right ventricle (downstream). The frame comprises a strutted atrial dome that conforms to the atrium without obstruction of blood flow from the incoming great veins (i.e. superior vena cava and inferior vena cava) or other anomalous veins and/or tributaries. The frame further comprises ventricular struts to be placed within the right ventricle to secure the neo-prosthetic valve in a desired position. The assembly of the frame and valve is collapsible so that prior to deployment the assembly is placed in a vascular catheter, and then self-expands upon release in the heart.

28 Claims, 10 Drawing Sheets

(56) References Cited

U.S. PATENT DOCUMENTS

| | | | |
|---|---|---|---|
| 8,016,882 B2* | 9/2011 | Macoviak | A61F 2/2445 623/2.36 |
| 8,038,708 B2* | 10/2011 | Case | A61F 2/2475 623/1.24 |
| 8,784,482 B2* | 7/2014 | Rahdert | A61B 17/00234 623/2.36 |
| 9,173,737 B2* | 11/2015 | Hill | A61F 2/2457 |
| 9,872,765 B2* | 1/2018 | Zeng | A61F 2/2412 |
| 10,149,759 B2* | 12/2018 | Naor | A61F 2/2418 |
| 10,383,725 B2* | 8/2019 | Chambers | A61F 2/2418 |
| 11,504,229 B2* | 11/2022 | Oba | A61F 2/2418 |
| 2007/0156233 A1* | 7/2007 | Kapadia | A61F 2/2418 623/2.11 |
| 2008/0065204 A1* | 3/2008 | Macoviak | A61F 2/2454 623/2.17 |
| 2008/0140190 A1 | 6/2008 | Macoviak et al. | |
| 2010/0036479 A1* | 2/2010 | Hill | A61F 2/2457 623/1.26 |
| 2010/0280606 A1* | 11/2010 | Naor | A61F 2/2418 623/2.18 |
| 2012/0101571 A1* | 4/2012 | Thambar | A61F 2/2418 623/2.17 |
| 2012/0165928 A1* | 6/2012 | Nitzan | A61F 2/2412 623/2.15 |
| 2012/0271398 A1* | 10/2012 | Essinger | A61F 2/2412 623/1.11 |
| 2014/0031928 A1* | 1/2014 | Murphy | A61F 2/2418 623/2.37 |
| 2015/0094802 A1* | 4/2015 | Buchbinder | A61F 2/2454 623/2.38 |
| 2016/0113768 A1* | 4/2016 | Ganesan | A61F 2/2436 623/2.17 |
| 2016/0166382 A1* | 6/2016 | Nguyen | A61F 2/246 623/2.17 |
| 2016/0235529 A1* | 8/2016 | Ma | A61F 2/2418 |
| 2017/0100241 A1* | 4/2017 | Modine | A61F 2/2412 |
| 2017/0128203 A1* | 5/2017 | Zhang | A61F 2/2436 |
| 2017/0239041 A1* | 8/2017 | Quinn | A61F 2/2412 |
| 2018/0325662 A1* | 11/2018 | Modine | A61F 2/2418 |

FOREIGN PATENT DOCUMENTS

| | | | | |
|---|---|---|---|---|
| WO | WO-2014181336 A1 * | 11/2014 | | A61F 2/2409 |
| WO | WO-2018131043 A1 * | 7/2018 | | A61F 2/2415 |
| WO | WO-2019169087 A1 * | 9/2019 | | A61F 2/2409 |

* cited by examiner

TRANSCATHETER SELF-EXPANDABLE TRICUSPID VALVE REPLACEMENT SYSTEM

FIELD

The present technology relates to the treatment of cardiac valve regurgitation.

BACKGROUND

Cardiac valve regurgitation can cause acute and chronic symptoms (e.g. shortness of breath, intolerance, leg swelling, abdominal discomfort, malnutrition) and lead to considerable morbidity (e.g. acute pulmonary edema, heart failure, pulmonary hypertension, organ dysfunction, cachexia, anorexia) and mortality. Open-heart valve surgery has proven effectiveness but is associated with perioperative mortality and post-operative complications. Many patients may not be eligible for such a traumatic procedure, which entails long periods (months) of recovery time after open-heart surgery. Therefore, there exists a need for a less invasive procedure for treating the tricuspid valve between the right atrium and the right ventricle.

Currently, treatment for tricuspid regurgitation includes the use of a valve repair system named TriAlign, developed from the MitrAlign system, which uses intravascular transcatheter placement of sutures and pledgets to reshape (annuloplasty) morphology of the target valve, reducing the annulus circumference, the valve orifice area and the valve area. However, the TriAlign system is a repair system and not a replacement system. Additionally, current treatments for tricuspid regurgitation may include use of a mitral valve repair system, for example MitraClip, which has been used off-label for tricuspid valve repair. However, mitral valve repair systems are not intended or designed for use on the tricuspid valve, and are not FDA approved for such indication. Further, the use of such mitral valve repair systems requires deployment of one or multiple devices due to the trileaflet anatomy of the tricuspid valve, as opposed to the bileaflet nature of the mitral valve on which the MitraClip system is intended to be used. Accordingly, the use of a mitral valve repair system for treatment for tricuspid regurgitation is restricted to a limited number of cases in which valve and cardiac anatomy are deemed amenable, and may still have issues related to safety and efficacy. Therefore, there exists a need for a dedicated tricuspid replacement device and related procedure for patients who are ineligible or non-candidates for open-heart surgery.

SUMMARY OF THE INVENTION

The present technology is directed toward a tricuspid valve apparatus with a frame and an associated neo-prosthetic valve. The frame acts as a stabilizing structure that extends cephalad into the morphologic or functional right atrium (upstream) and caudally into the morphologic or functional right ventricle (downstream). The frame comprises a strutted atrial dome that conforms to the atrium without obstruction of blood flow from the incoming great veins (i.e. superior vena cava and inferior vena cava) or other anomalous veins and/or tributaries. The frame further comprises ventricular struts which are placed within the right ventricle to secure the neo-prosthetic valve in a desired position. The assembly of the frame and valve is collapsible so that prior to deployment, the assembly is placed in a vascular catheter, and then self-expands upon release in the heart (cardiac chambers).

BRIEF DESCRIPTION OF THE DRAWINGS

The disclosure will be readily understood by the following detailed description in conjunction with the accompanying drawings, wherein like reference numerals designate like structural elements, and in which.

DETAILED DESCRIPTION

Throughout this description for the purposes of explanation, numerous specific details are set forth in order to provide a thorough understanding of the many aspects and embodiments disclosed herein. It will be apparent, however, to one skilled in the art that the many aspects and embodiments may be practiced without some of these specific details. In other instances, known structures and devices are shown in diagram or schematic form to avoid obscuring the underlying principles of the described aspects and embodiments.

The present technology is in the technical field of tricuspid valve regurgitation. In particular, the present technology is in the field of transcatheter placement of a self-expandable device for the purpose of tricuspid valve structure and/or function replacement. Placement of embodiments of the devices as disclosed herein to replace the function of the native tricuspid valve and/or structures in close proximity to the tricuspid valve, and allows for the restoration of right-sided heart function and/or reversal of pathophysiology associated with severe tricuspid regurgitation. The device may be deployed, for example, under fluoroscopy (e.g.

X-ray), or an alternative energy source (e.g. ultrasound) for guidance that can image the position and function of the device, and/or using surgical navigation systems.

Embodiments of the device may be deployed via a vascular catheter (transcatheter approach), or may also be deployed and placed using an alternative approach as deemed clinically and technically feasible by the operating interventionalist or surgeon. Embodiments of the device may be suited for clinical settings where open-heart surgery or cardiothoracic surgery is contraindicated, at least initially. For example, the described devices may be suitable for palliative indications, as in patients with advanced, including end-stage, right heart disease, right heart failure, portal hypertension secondary to cardiac cirrhosis, and/or systemic organ or multiorgan dysfunction and failure (e.g. enteropathy, severe ascites, lymphedema). Such palliation may improve patient symptoms (primary aim) and potentially extend life expectancy (possible collateral benefit). Placement or implantation of these devices are not limited to the adult patient population, and may be used in the pediatric population.

Figure 2A:
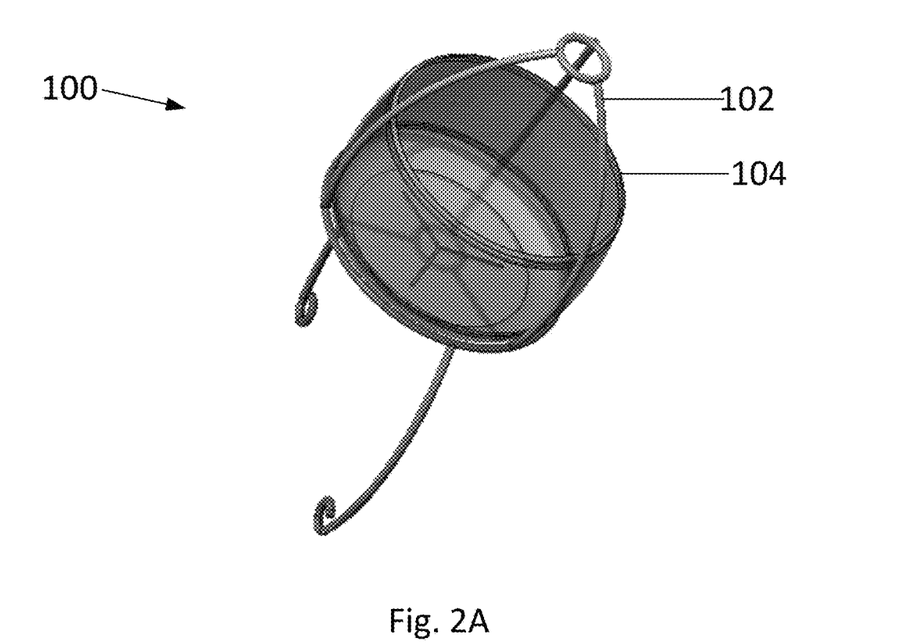
FIG. 2A shows a perspective view of a tricuspid valve replacement system according to embodiments of the present technology.
Figure 2B:
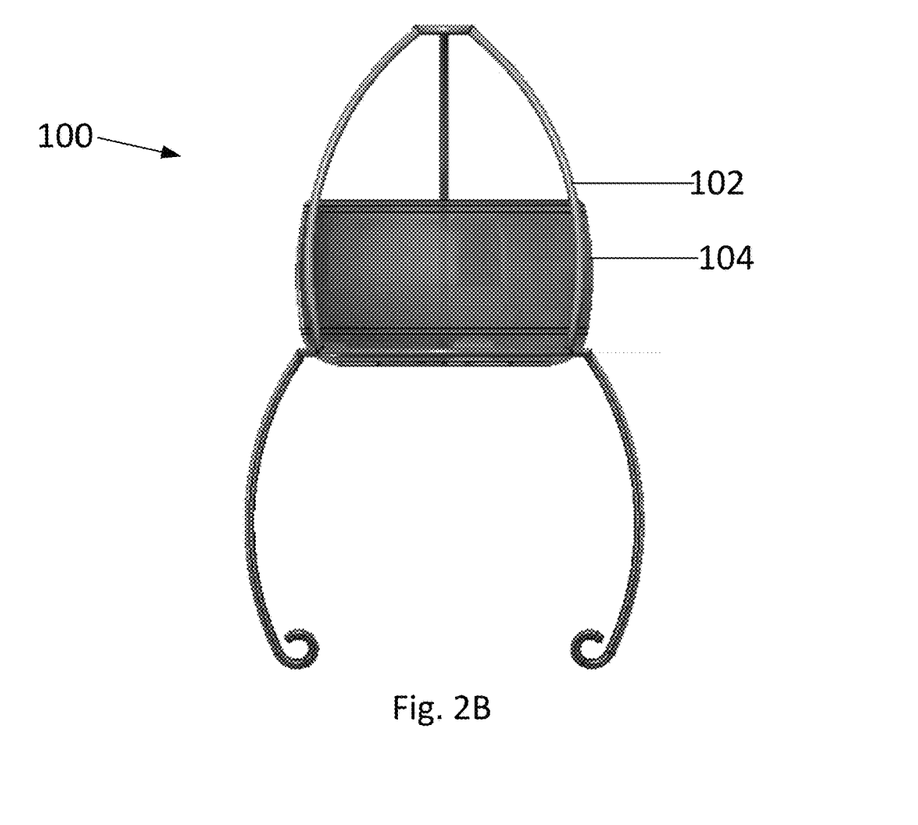
FIG. 2B shows a front view of the tricuspid valve replacement system of FIG. 2A.

FIG. 2A shows a perspective view and FIG. 2B shows a front view of a tricuspid valve replacement system 100, also referred to as device 100, according to embodiments of the technology. As shown, the system 100 comprises a frame 102 and a valve 104 coupled to the frame 102.

Figure 3A:
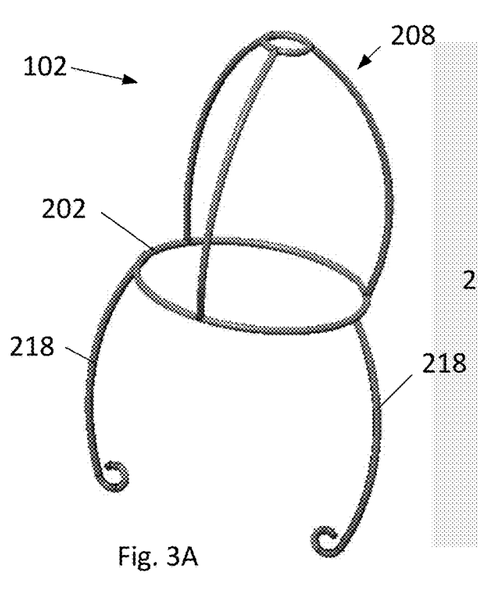
FIGS. 3A-3C shows perspective views of a frame of a tricuspid valve replacement system according to the present technology.
Figure 3B:
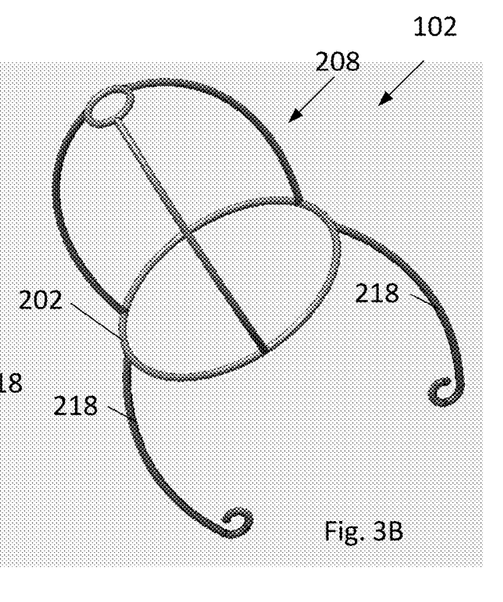
Figure 3C:
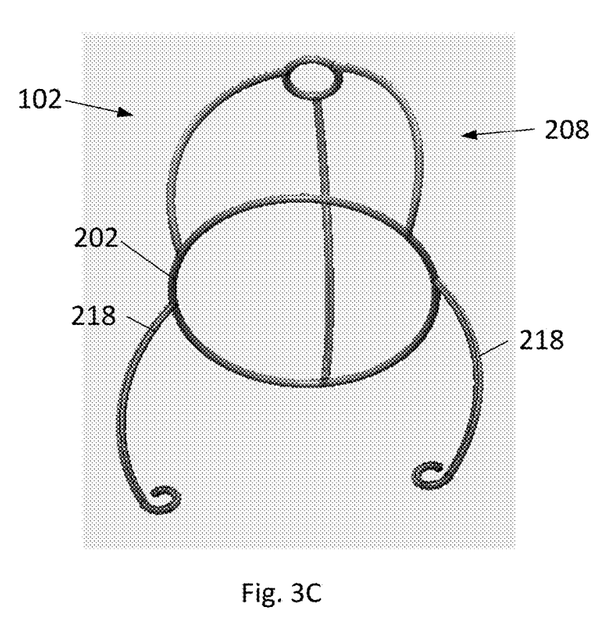
Figure 3D:
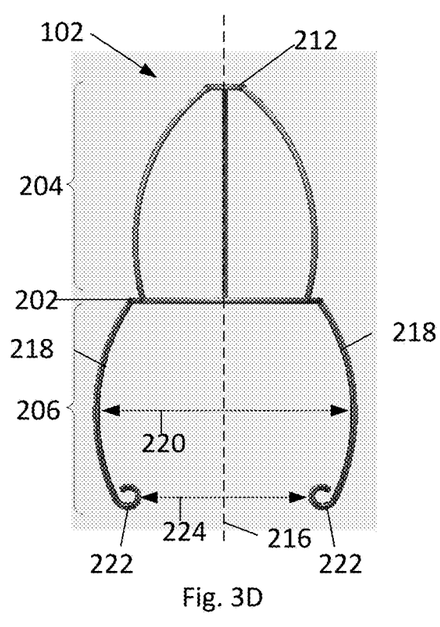
FIGS. 3D and 3E show front views of a frame of a tricuspid valve replacement system according to embodiments of the present technology.
Figure 3E:
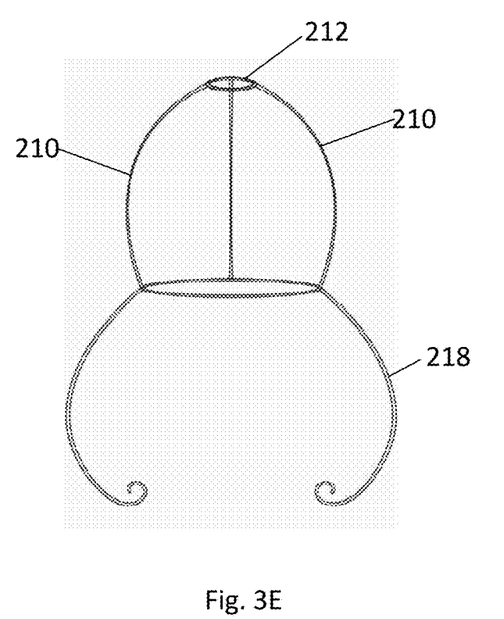

FIGS. 3A-C show perspective views of a frame 102 of a tricuspid valve replacement system 100 according to embodiments of the technology. As shown in FIG. 3D the frame 102 comprises a central ring 202, an atrial end 204 extending from an upper/atrial side of the central ring 202, and a ventricular end 206 extending from a lower/ventricular side, opposite the upper side, of the central ring 202.

The frame 102 is shown in FIGS. 3A-H in an expanded state, wherein the expanded state is the form the frame 102 exhibits when not acted upon by outside forces. When deformed the frame 102 is designed to self-expand toward the expanded state when outside forces are reduced or eliminated, for example when a mechanism of restraint is released. As will be discussed in greater detail below, the elements of the frame 102 are designed to be resilient and conform to various sized cavities that the frame is placed within during use, for example inside of a catheter or within various portions of the heart.

Central Ring

The central ring 202 is sized to be placed within or near the annulus of the tricuspid valve of a human patient. As shown for example in FIGS. 3G and 3H, the central ring 202 may be substantially circular in shape in the expanded state. In embodiments, the central ring 202 may be elliptical or other round shapes. In embodiments, in the expanded state the central ring 202 may be planar, or may be non-planar, for example the central ring may be defined on the surface of a hyperbolic paraboloid (i.e. saddle shaped). The central ring 202, and other portions of the frame 102, may be formed of a wire with a gauge/diameter between 0.2 mm and 0.8 mm, preferably 0.5 mm. The rigidity of the central ring 202, or portions therefore, are selected so that in a placement state, when the frame 102 is placed within the heart and acted upon by normal forces from walls within the heart, the shape of the central ring 202 corresponds to the shape and size of the annulus of the tricuspid valve.

Embodiments of frames 102 may have central rings 202 with different sizes/diameters for different sized annuli of tricuspid valves. The circumference of the tricuspid annulus in normal subjects is for example about 120 mm, and in subjects with tricuspid regurgitation (i.e. a diseased state) the circumference may be between 140 mm and 150 mm, or greater. In severe tricuspid regurgitation the average diameter of the tricuspid annulus may be >35 mm, whereas a normal subject the average diameter may be 28±5 mm. Further, in a diseased subject the right heart may be very dilated or engorged. The circumference, i.e. length of the perimeter, of embodiments of central rings 202 may be between 45 mm and 120 mm and has an average diameter in the expanded state between 15 mm and 40 mm.

Atrial Dome

The frame 102 further comprises an atrial dome 208 extending from the atrial end 204 of the central ring 202. The atrial dome 208 comprises a plurality of atrial struts 210 extending from the central ring 202 to an atrial end of the frame 102. As shown in the top view of FIG. 3G, in embodiments, the atrial dome 208 may comprise three atrial struts 210. In embodiments, the atrial dome 208 may comprise 2, 3, 4, or more atrial struts 210. More atrial struts 210 provide the advantage of a more stable device, however, more atrial struts 210 also increases the size of catheter needed to house the device in the collapsed delivery state and increases risk of complications associated with greater surface area of a foreign body in the heart.

In embodiments, the atrial struts 210 terminate at the atrial end at an end ring 212. As will be discussed below, the end ring 212 may receive a guide wire during placement of the frame 102. The end ring 212 may have an inner diameter of 5 mm to 10 mm.

In embodiments, the atrial end may not comprise an end ring 212 and the atrial struts 210 may be coupled together at an intersection. In embodiments, with an even number of atrial struts 210, two opposing atrial struts 210 may be formed from the same wire, and the tops of loops forming pairs of atrial struts 210 overlap to define the atrial end.

The length of the atrial dome 208 from the central ring 202 to the atrial end corresponds to the length of the right atrium of the human patient. Patients with tricuspid regurgitation, and other right-sided cardiac or cardiopulmonary diseases, including severe pulmonary hypertension, may have enlarged right atria. To select an appropriately sized atrial dome 208 to correspond to the enlarged atrium of a patient, pre-procedural imaging (e.g. computer tomography, cardiac magnetic resonance, ultrasonography) of the patient may be used to determine a measured length and diameter of the enlarged atrium. As shown in FIGS. 3A-H, in embodiments the atrial struts 210 are bowed outwardly so that the maximum diameter 214 (shown in the dashed circle in FIG. 3G) of the atrial dome 208 is greater than the diameter of the central ring 202. In embodiments, each atrial strut 210 bows in a plane that is parallel to and extends through the central axis 216 of the frame 102.

During use in a heart, the atrial dome 208 is placed within the right atrium with the central ring 202 placed within or directly above a plane of the annulus of the tricuspid valve. The outer surfaces of the atrial struts 210 defining the atrial dome 208 are intended to contact the walls of the right atrium in order to maintain the position of the central ring 202 at a fixed position relative to the annulus of the tricuspid.

In the expanded state the atrial struts 210 have an intrinsic level of rigidity, depending on the composition and malleability of the metal or metal alloy, such that in the placement state the atrial struts 210 are able to continually deform or conform according to the dynamic shape of the anatomy of the right atrium during the pumping of the heart, and with movement of the heart. In embodiments, each atrial strut 210 of the frame 102 has the same length. In embodiments, the atrial struts 210 of a frame may have different lengths and/or levels of rigidity to correspond to the asymmetrical shape of the right atrium.

Ventricular Struts

The frame 102 comprises a plurality of ventricular struts 218 extending from the ventricular side of the central ring 202. As shown in FIGS. 3A-3H, in embodiments, the frame 102 comprises two ventricular struts 218. In embodiments, the frame may comprise 3 or more ventricular struts 218.

In embodiments, the ventricular struts 218 terminate separately from each other at a ventricular end of the frame 102. During placement in the heart, the ventricular end is positioned toward the inferoapical aspect of the right ventricle. The ventricular struts 218 bow outwardly so that the maximum distance 220 between the ventricular struts 218 at the point of maximum bowing away from a central axis 216 of the frame 102 is greater than the diameter of the central ring 202. The maximum distance of the ventricular struts 218, may be wider than the maximum diameter of the atrial dome 208 in order to be situated in the right ventricle when the right ventricle is larger than the right atrium. Further, in patients with right atrial enlargement the right atrium may be larger than the right ventricle and the maximum diameter of the atrial dome 208 may be larger than the maximum distance of the ventricular struts 218. During use, the ventricular struts 218 are placed within the right ventricle with the central ring 202 placed within the annulus of the tricuspid valve. The outer surfaces of the ventricular struts 218 contact the walls of the right ventricle in order to maintain the position of the central ring 202 within the annulus of the tricuspid. Both the atrial dome 208 and the ventricular struts 218 maintain the position and orientation of the frame 102 within the heart.

Figure 3F:
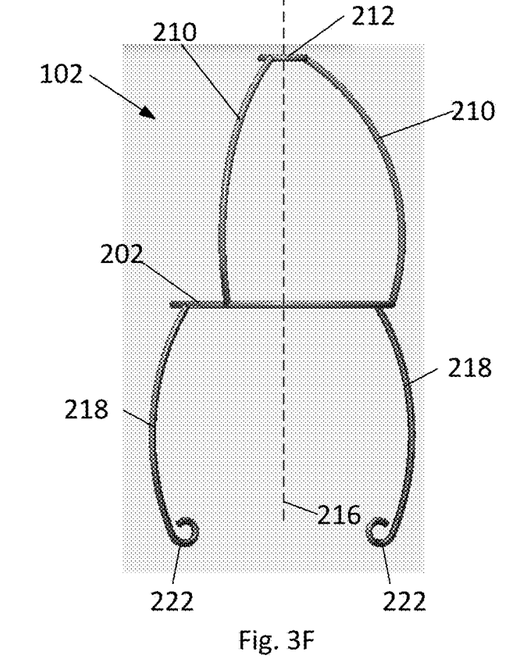
FIG. 3F shows a side view of a frame of a tricuspid valve replacement system according to embodiments of the present technology.

The ventricular struts 218 terminate at atraumatic ends 222, which may be pigtail-like in geometry, as shown for example in FIGS. 3D and 3F. The atraumatic ends 222 are configured not to damage/puncture the walls of the ventricle. In embodiments, the atraumatic ends 222 are formed by curling the end of the wire forming the ventricular strut 218 so that other portions of the strut obscure the tip of the wire so that that sharp tip is not exposed and therefore not able to contact a ventricle wall surface.

Figure 1:
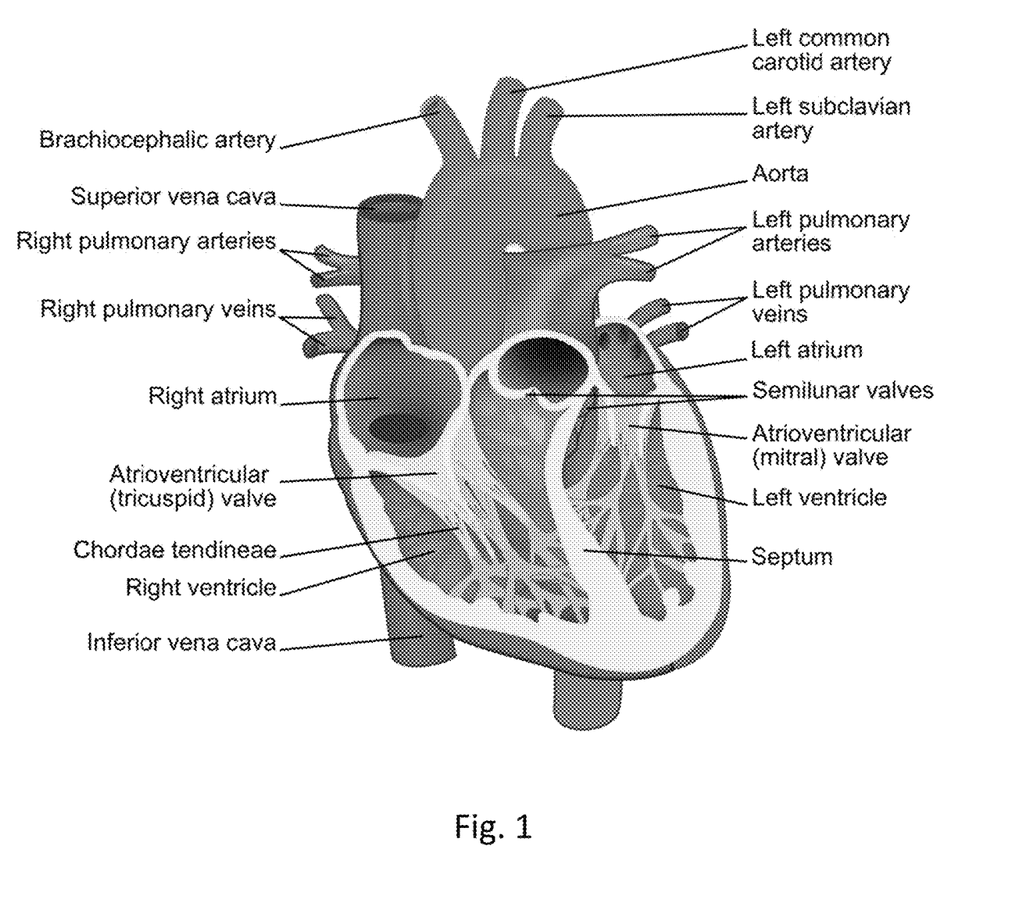
FIG. 1 shows an annotated diagram of a heart.

The distance each ventricular strut 218 extends from the central ring 202 may correspond to the length of the right ventricle of the human patient by being of similar length or shorter. In embodiments, the distance is between 50 mm and 60 mm. The gap 224 between the atraumatic ends 222 is sized to avoid contact and entanglement with the chordae tendineae of the right ventricle, for example as shown in the annotated diagram of the heart in FIG. 1.

The view of the ventricular struts 218 in FIG. 3D shows the expanded state of the frame 102. The rigidity of the ventricular struts 218 is selected so that in the placement state the ventricular struts 218 are able to conform to the dynamic shape of the anatomy the right ventricle. In embodiments, each ventricular strut 218 has the same length. In embodiments, the ventricular struts 218 of a frame 102 may have different lengths and/or levels of rigidity in order to correspond to the asymmetric shape of the right ventricle.

Figure 3G:
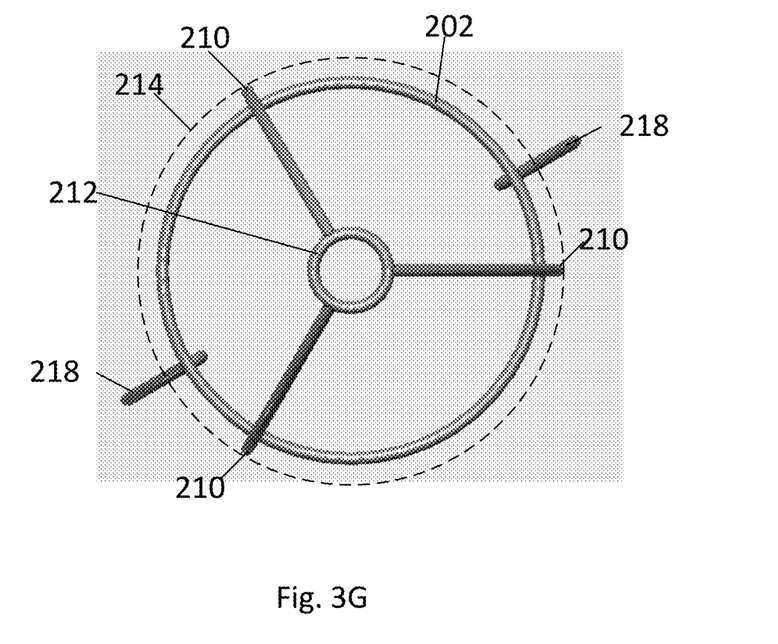
FIG. 3G shows a top view of a frame of a tricuspid valve replacement system according to embodiments of the present technology.
Figure 3H:
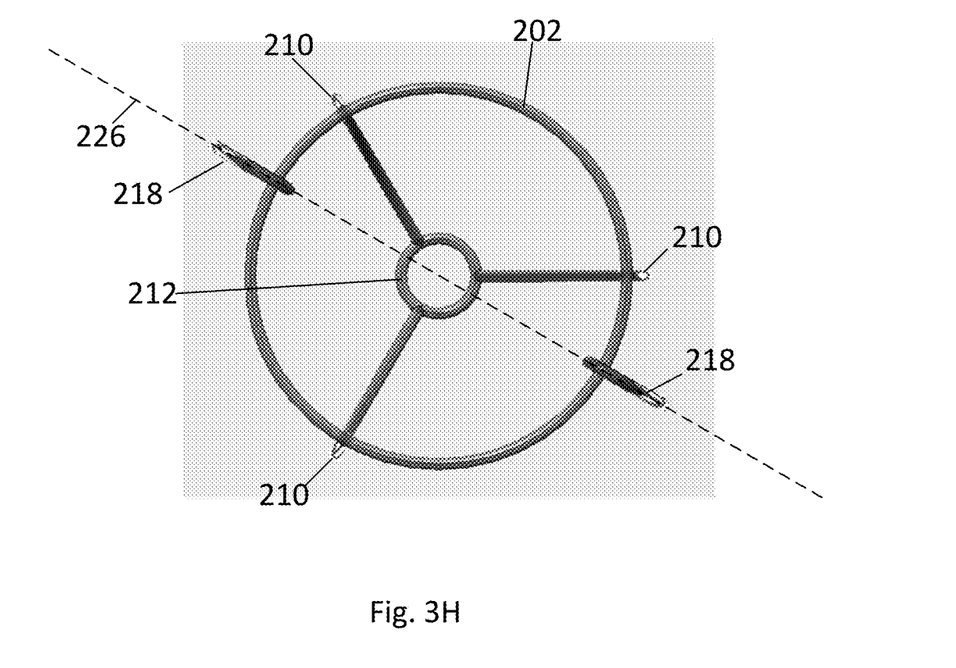
FIG. 3H shows a bottom view of a frame of a tricuspid valve replacement system according to embodiments of the present technology.

The ventricular struts 218 may be bowed in the same plane as each other, and define a ventricular strut plane 226, as shown in FIG. 3H. In embodiments, the ventricular struts 218 may bow in a non-planar manner, i.e. have shapes that do not lie in a single plane.

Strut Arrangement

FIGS. 3G and 3H illustrate the top and bottom aspects of the frame 102 and the orientations of the atrial struts 210 and ventricular struts 218 relative to the central ring 202.

In embodiments, the atrial struts 210 are positioned uniformly around the perimeter of the atrial side of the central ring 202. For example, in embodiments with a circular central ring 202 and three atrial struts 210, as shown in FIG. 3G, the atrial struts 210 are spaced with 120-degree intervals between adjacent atrial struts 210. Further, as shown in FIG. 3H, in embodiments, the ventricular struts 218 may be on opposite sides of the central ring 202, i.e. 180 degrees, from each other. Further, the ventricular struts 218 may be spaced apart from the atrial struts 210 so that an atrial strut 210 is not directly opposite a ventricular strut 218 on the central ring 202. For example, as shown in FIGS. 3G and 3H each ventricular strut 218 is spaced 30, 90, and 150 degrees from the three atrial struts 210, respectively.

Valve

Figure 4A:
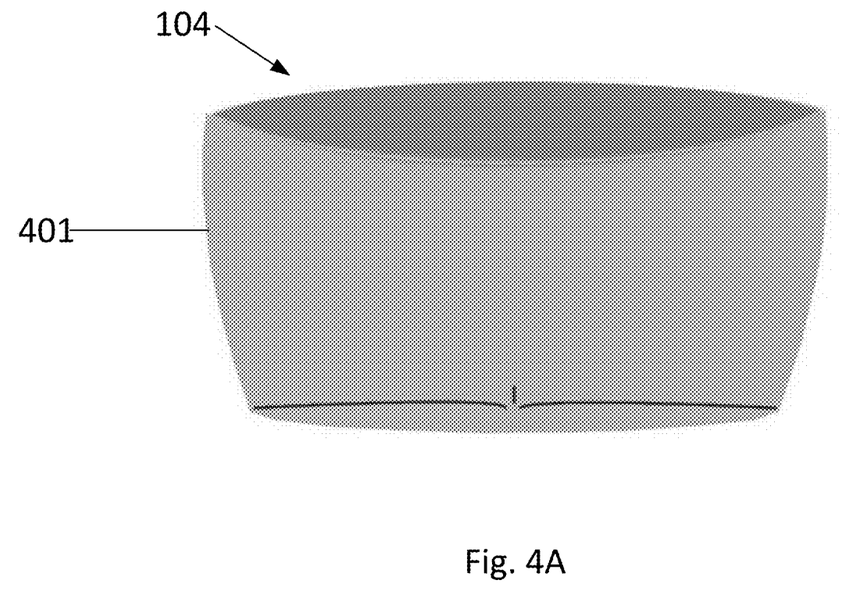
FIGS. 4A and 4B show a valve of a frame of a tricuspid valve replacement system according to embodiments of the present technology.
Figure 4B:
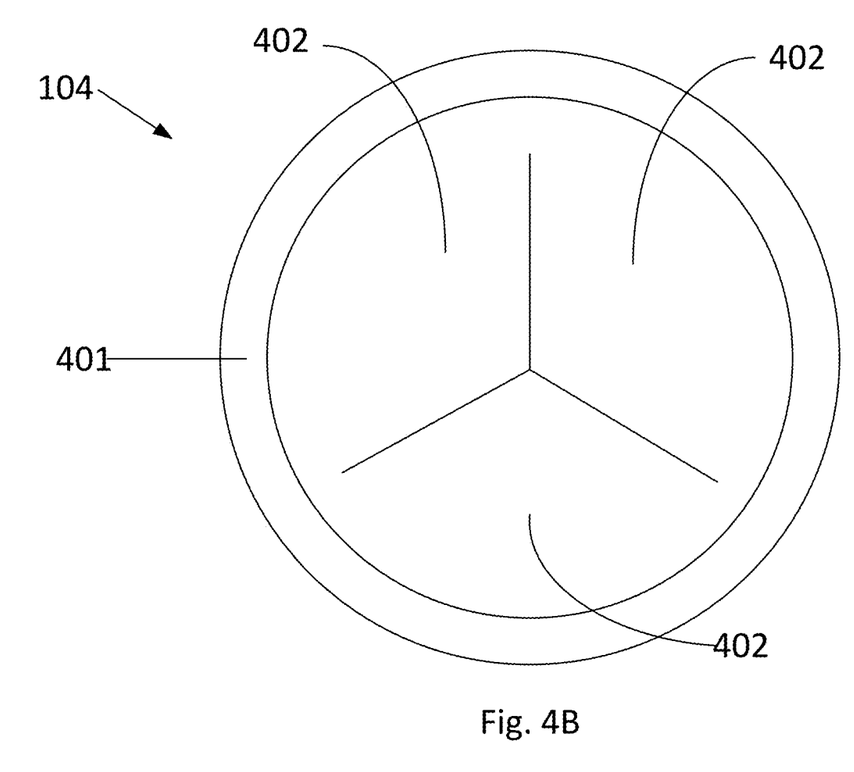

FIGS. 4A and 4B show a side lateral aspect and a bottom inferior aspect, respectively, of the valve 104. The valve 104 may comprise a bovine pericardial support and buttress 401, and a tissue pericardial valve with three neo-valve leaflets 402. As shown, the pericardial support and buttress 401 may be conical and may form a support layer to channel flow above the plane of the neo-valve leaflets 402. The pericardial support and buttress 401 may contribute to maintaining the structure and rigidity of the neo-valve leaflets 402. The base dimensions of the valve 104 are selected to correspond to the dimensions of the central ring 202 of the frame 102, so that the valve 104 is positioned within the central ring 202.

Manufacture.

In embodiments, the frame 102 is self-expanding and may be made of a shape-memory alloy. For example, the frame 102 may be composed of a nickel titanium (nitinol) alloy. The frame 102 may have a wire gauge of 0.5 mm. Components and composition of the frame 102 may be of different sizes, thicknesses (wire gauge) and/or materials.

The components of the frame 102, including the struts and rings, may be individually preformed into the desired shape in the expanded state (shape memory effect), and then coupled together to form a unitary structure. The components of the frame 102 may be coupled together, for example, with adhesive and/or welding.

Figures 5A, 5B, 5D:
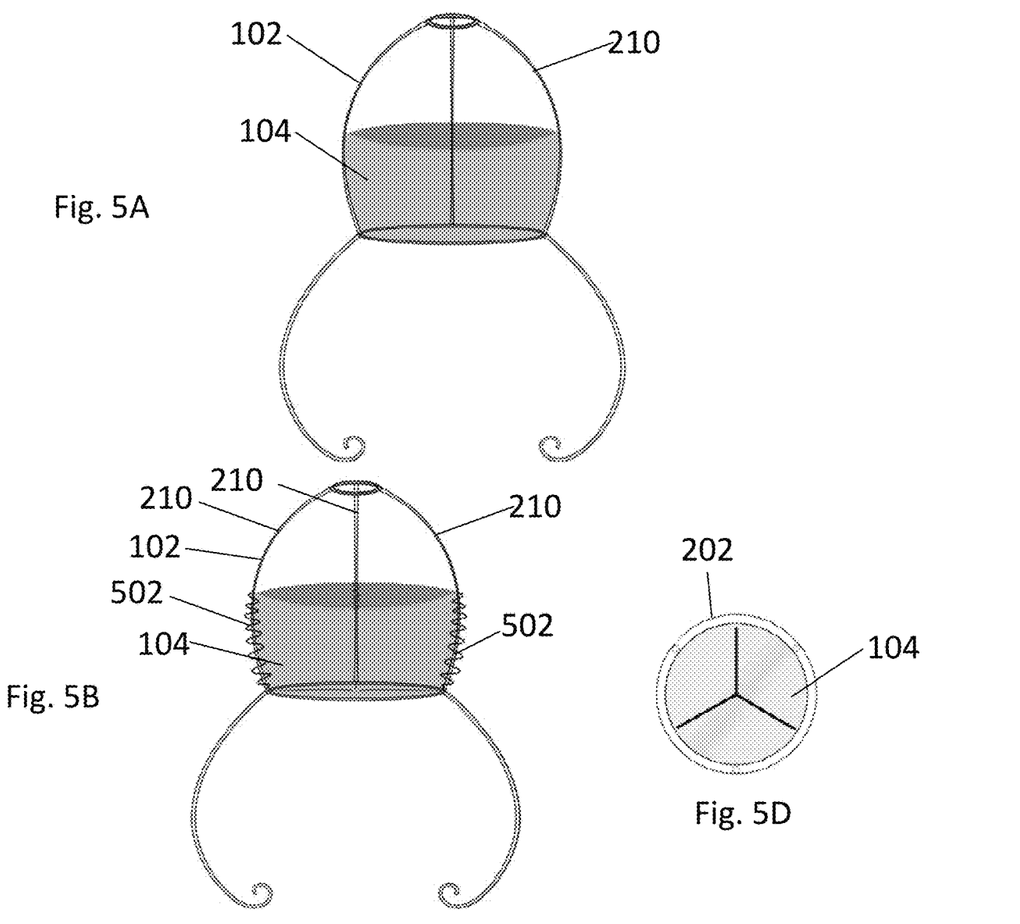
FIGS. 5A-E show steps of a manufacturing process of a tricuspid valve replacement system according to embodiments of the present technology.
Figures 5C, 5E:
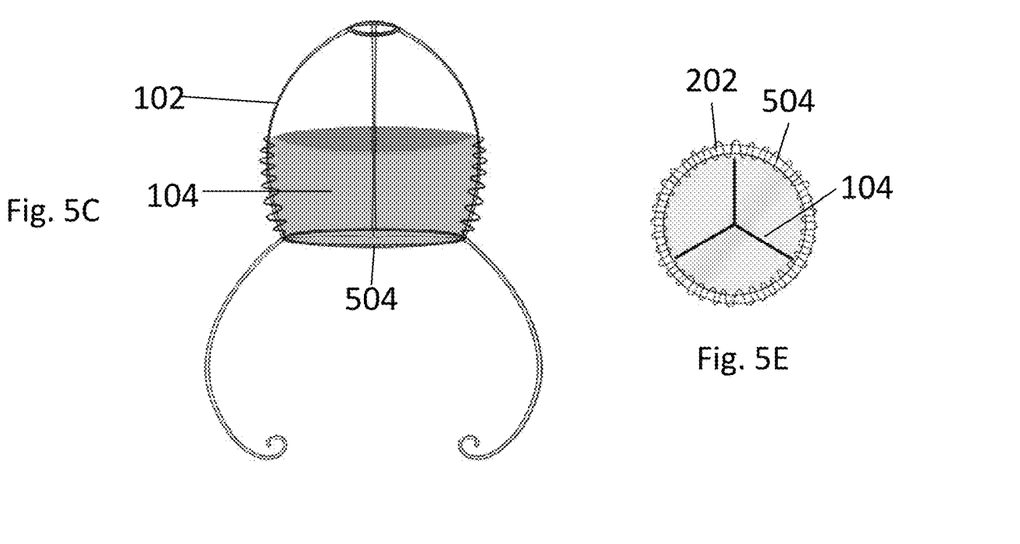

In embodiments, the lower perimeter of the valve 104 is sewn to the central ring 202, and portions of the sidewalls of the valve 104 are sewn to the atrial struts 210. FIG. 5A-E shows step of assembling the tricuspid valve replacement system 100. As shown in FIG. 5A, the valve 104 may be placed with the atrial dome 208 of the frame 102 with the plane of the leaflets of the valve 104 substantially coincident with the plane of the central ring 202. The valve 104 may be initially attached to the frame 102 by suturing 502 the sidewall of the valve 104 to each atrial strut 210, as shown in FIGS. 5B and 5D. Next, the lower perimeter of the valve 104 may be sutured 504 to the central ring 202 as shown in FIGS. 5C and 5E. In embodiments, the valve 104 may be coupled to the frame 102 in other manners, for example with adhesive.

In embodiments, the frame 102 may have a coating to modify the biological response to the foreign body. For example, the coating may include antithrombotics (e.g. heparin).

Catheter

Figure 6A:
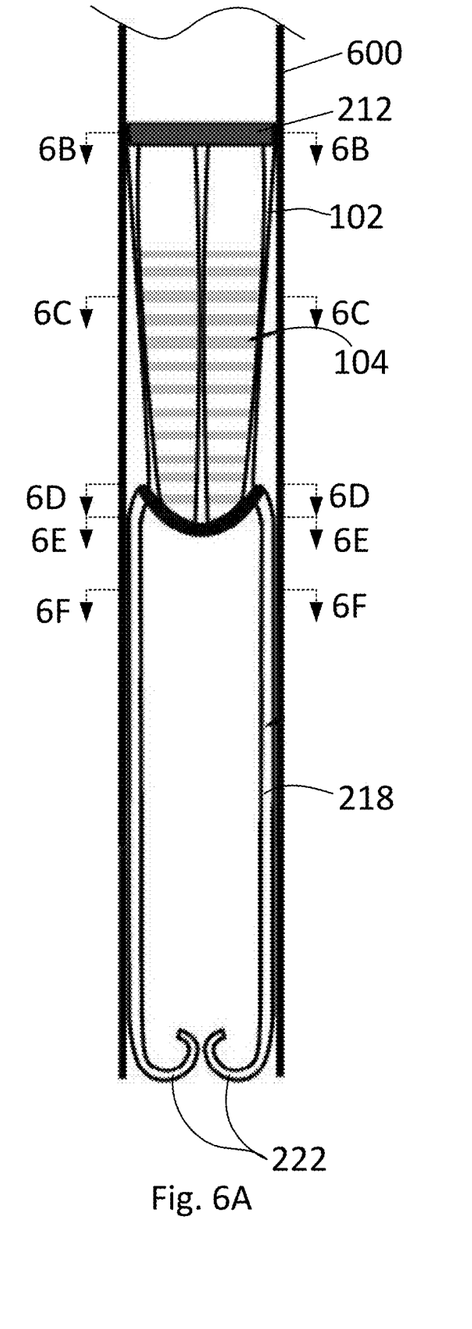
FIGS. 6A-F show a tricuspid valve replacement system in a collapsed state inside a catheter according to embodiments of the present technology.
Figure 6B:
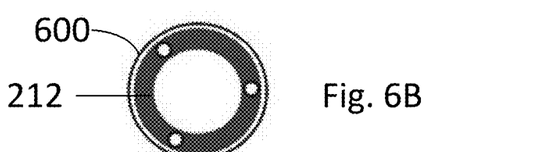
Figure 6C:
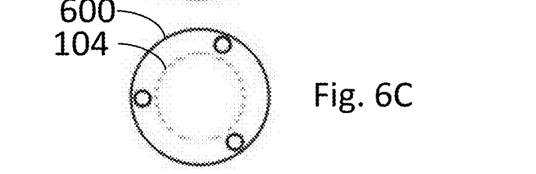
Figure 6D:
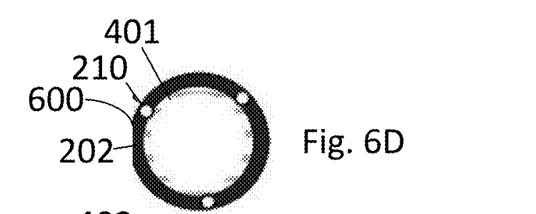
Figure 6E:
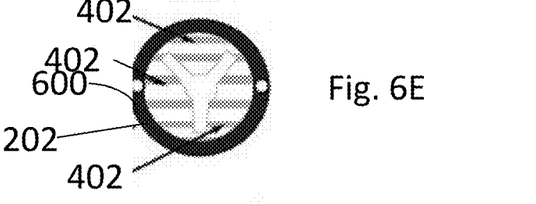
Figure 6F:
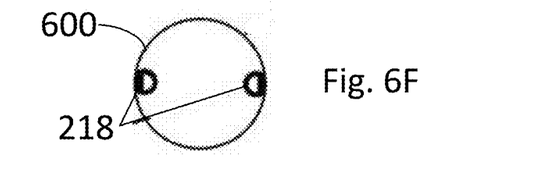

FIG. 6A shows the tricuspid valve replacement system 100 in the collapsed state inside a catheter 600, and FIGS. 6B-6F show cross-sections thereof at different levels within the catheter.

As shown in FIG. 6A, the frame 102 is oriented in line with the longitudinal axis of the catheter 600 with the collapsed atrial dome 208 distal and the collapsed ventricular struts 218 proximal to the distal opening of the catheter 600. The catheter may be a 6 mm to 7 mm gauge, 18 French (Fr) to 21 Fr. In the collapsed state, the central ring 202 may be folded, and/or helically twisted, and the prosthetic neo-valve may be furled and/or folded to enable the device to be stowed inside the catheter. In the collapsed state the atrial struts 210 are straightened so that the elongated collapsed atrial dome 208 is positioned within the catheter 600. In embodiments, the diameter of the catheter 600 and the end ring 212 are selected so that the end ring 212 is not deformed in the collapsed state so that a guide wire, as will be discussed below, can pass through the end ring 212. In the collapsed state the ventricular struts 218 are straightened so that the atraumatic ends 222 are near each other, contact, or overlap within the catheter 600. In the collapsed state the valve 104 is folded or rolled up within the collapsed atrial dome 208.

Method

FIG. 7A-D show method steps of positioning the tricuspid valve replacement system 100 within the heart 700. In embodiments, the system may be placed by intravascular transcatheter deployment. However, placement of the device is not limited to transcatheter deployment. For example, the device may be placed via open-heart surgery.

Prior to placement of the device 100, cardiovascular imaging for example, computed tomography (CT), cardiac magnetic resonance imaging (MM), and ultrasonography, may be used to determine the suitability of a patient's cardiac anatomy and inform the size and shape of the tricuspid annulus, right atrium, and right ventricle. For example, the use of pre-procedural (CT) and/or cardiac (MM) during Heart Team planning may potentially improve post-procedural outcomes and success. Further, 3-dimensional (3D) imaging and/or 3D printing guidance may be used to plan the orientation of the physical device within a 3-D model prior to performing the procedure. These pre-operative steps may be used to maximize procedural success and reduce post-procedural complications including paravalvular leak or peri-device flow leak, device dislodgement and/or suboptimal placement. Intra-procedurally, ultrasound guidance (e.g. transesophageal echocardiography (TEE), intracardiac echocardiography (ICE)) on top of fluoroscopy may also be used to enhance apparatus positioning and placement. Based on available data from imaging, a best fit frame 102 and valve 104 of the appropriate shape and size may be selected.

With appropriate preprocedural planning, the correctly sized device 100 is placed in the collapsed state and placed within the end of a catheter 702.

Figure 7A:
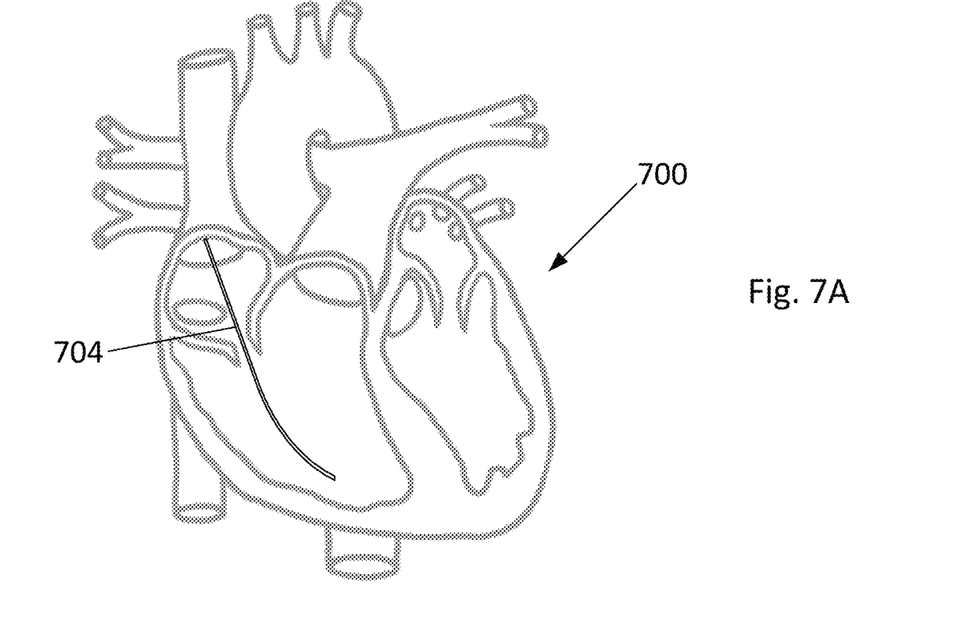
FIGS. 7A-7D show a placement procedure of a tricuspid valve replacement system according to embodiments of the present technology.
Figure 7B:
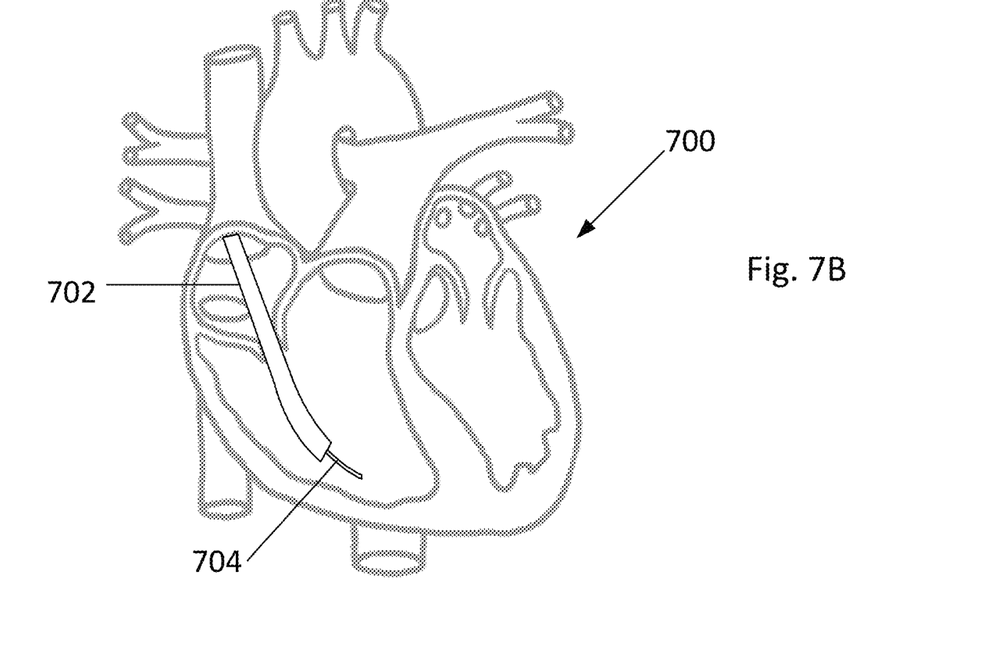

The catheter 702 loaded with the device 100 is advanced into the superior vena cava (if accessing via the transjugular vein approach) or the inferior vena cava (if accessing via the transfemoral vein approach) en route to the right atrium. In embodiments, prior to inserting the catheter 702, a guide wire 704 is first inserted through the superior or inferior vena cava, through the right atrium, through the tricuspid annulus and into the right ventricle, as shown in FIG. 7A. The guide wire 704 may then be used to introduce the delivery catheter 702 holding the device 100 in the collapsed state into the heart, as shown in FIG. 7B. The delivery catheter 702 and device 100 may extend over the guide wire 704 so that the guide wire extends through the central ring 202, opening in the valve between the neo-valve leaflets 402, and end ring 212.

Using cardiac imaging, the distal end of catheter 702 loaded with the device 100 is positioned to a deployment position so that the collapsed central ring 202 is within or slightly above the tricuspid annulus, the collapsed ventricular struts 218 are positioned within the right ventricle, and the collapsed atrial dome 208 is within the right atrium. The distal end of the catheter 702 with the collapsed device 100 may be rotated so that when expanded the ventricular strut plane 226 and the frame 102 are in the desired rotational position around the axis of the device 100. In embodiments, after deployment and self-expansion of the frame 102, the frame 102 may be oriented in a desired rotational position within the heart 700.

Figure 7C:
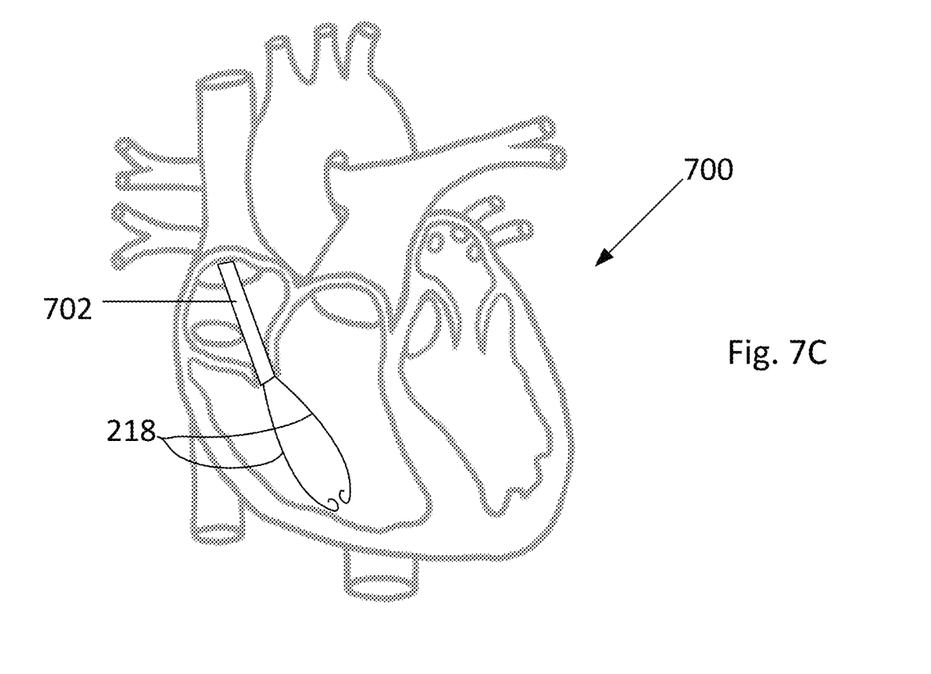
Figure 7D:
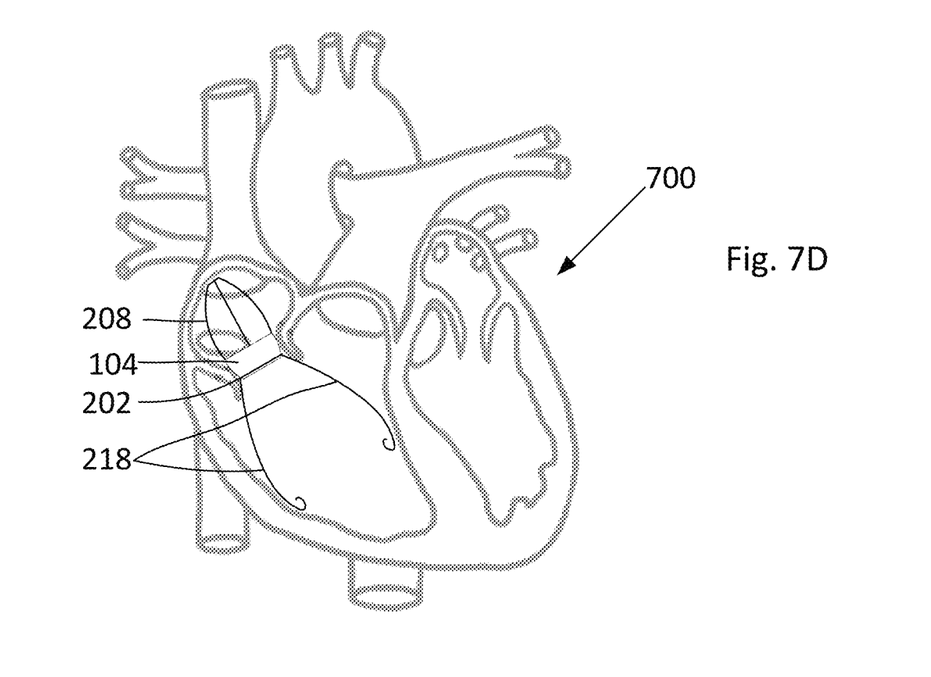

After the catheter 702 is deployed in the placement position, the catheter 702 is withdrawn by pulling the catheter 702 back while the device 100 is kept stationary. As the catheter 702 is withdrawn over the frame 102, the frame 102 will unwind and self-expand from the collapsed state to the expanded state. As the catheter 702 is withdrawn over the collapsed device 100 by pullback, the ventricular struts 218 expand and contact the walls of the right ventricle, as shown in FIGS. 7C and 7D. As the catheter 702 is further withdrawn, the central ring 202 expands with the annulus of the native tricuspid valve, holding or wedging the flaps of the native heart valve in an open position. As the catheter 702 is further withdrawn, the atrial dome 208 expands and contacts the walls of the right atrium, as shown in FIG. 7D. In embodiments, a guide wire may not be used in the method of placing the device.

In the delivered state shown in FIG. 7D the atrial end of the device 100 is positioned at the confluence of the superior vena cava and the inferior vena cava. In the delivered state the central ring 202 may rest on or abut the native tricuspid annulus, and the native tricuspid valve becomes plied open (or wedged open) and functionally replaced by the neo-prosthetic tricuspid valve 104.

After placement, through endothelialization and/or coverage by fibroblasts and fibrocytes, the atrial struts 210 will be sequestered over time and the device further anchored in place. The ventricular struts 218 continue to stabilize the device 100. While the heart is contracting with the device in place, the atraumatic (pigtail) ends of the ventricular struts 218 cushion the impact on the ventricle wall.

The procedure may be used to replace diseased native tricuspid valves of the heart including tricuspid regurgitation, mixed tricuspid regurgitation and stenosis, and congenital tricuspid valvular anomalies.

The procedure with the deployed device improves the physiology and abnormal hemodynamics associated with a diseased tricuspid valve. Further, the deployed device 100 restores the pressure gradients in the right heart and pulmonary and peripheral venous circulation, and ameliorates or reverses abnormal circulatory physiology in the venous system causing gut edema, ascites, congestive hepatopathy, transaminitis, peripheral edema, and other pathologies due to venous congestion from an abnormal tricuspid valve.

The various aspects, embodiments, implementations or features of the described embodiments can be used separately or in any combination. In particular, it should be appreciated that the various elements of concepts from FIGS. 2A-7D may be combined without departing from the spirit or scope of the invention.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, or gradients thereof, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained.

Preferred embodiments of this invention are described herein, including the best mode known to the inventors for carrying out the invention. The invention is susceptible to various modifications and alternative constructions, and certain shown exemplary embodiments thereof are shown in the drawings and have been described above in detail. Variations of those preferred embodiments, within the spirit of the present invention, may become apparent to those of ordinary skill in the art upon reading the foregoing description. The inventors expect skilled artisans to employ such variations as appropriate, and the inventors intend for the invention to be practiced otherwise than as specifically described herein. Accordingly, it should be understood that there is no intention to limit the invention to the specific form or forms disclosed, but on the contrary, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of specific embodiments are presented for purposes of illustration and description. They are not intended to be exhaustive or to limit the described embodiments to the precise forms disclosed. It will be apparent to one of ordinary skill in the art that many modifications and variations are possible in view of the above teachings.

The invention claimed is:

1. A tricuspid valve replacement system for use in a heart of a patient, comprising:
    a frame; and
    a valve coupled to the frame,
    wherein the frame comprises;
        a central ring,
        a plurality of atrial struts extending from a first side of the central ring and terminates at an atrial end of the frame thereby defining an atrial dome, wherein the plurality of atrial struts comprises between two and four atrial struts and
        two ventricular struts extending from a second side of the central ring opposite the first side to a ventricular end of the frame;
    wherein the frame defines a central axis,
    wherein the two ventricular struts terminate separately from each other at the ventricular end of the frame, wherein each of the two ventricular struts bow outwardly away from the central axis so that a maximum distance between the ventricular struts at a point of maximum bowing away from the central axis is greater than a diameter of the central ring,
    wherein the valve is coupled to the central ring and the plurality of atrial struts, and
    wherein the tricuspid valve replacement system is configured to be placed within the heart of the patient with the atrial dome positioned within a right atrium of the heart, the central ring and valve within an annulus of a native tricuspid valve of the heart, and the plurality of ventricular struts within a right ventricle of the heart so that atrial dome and the plurality of ventricular struts stabilize the tricuspid valve replacement system within the heart in order for the valve to replace function of the native tricuspid valve.

2. The system of claim 1, wherein the plurality of atrial struts comprise three and only three atrial struts.

3. The system of claim 2, wherein the three atrial struts bow away from the central axis of the frame so that a maximum diameter of the atrial dome is larger than a maximum diameter of the central ring.

4. The system of claim 3, wherein the frame further comprises an end ring configured to receive a guidewire to facilitate delivery and placement of the frame, and wherein the three atrial struts are coupled to and extend between the central ring and the end ring.

5. The system of claim 2, wherein the two ventricular struts each terminate at an atraumatic end with a curled end.

6. The system of claim 5, wherein the three atrial struts are uniformly positioned radially around the central ring,
    wherein the two ventricular struts are positioned radially at opposite sides of the central ring, and
    where the three atrial struts and two ventricular struts are positioned on the central ring in a non-overlapping manner.

7. The system of claim 1, wherein the tricuspid valve replacement system is configured to be placed in a collapsed state within a catheter for delivery into the heart.

8. The system of claim 7, wherein the atrial struts, ventricular struts and central ring are formed of a shape memory alloy wire and configured to self-expand so that the tricuspid valve replacement system self-expands from the collapsed state to a delivery state within the heart.

9. The system of claim 7, wherein an inner diameter of the catheter is less than 7 mm in diameter.

10. The system of claim 1, wherein the valve is sutured to the frame.

11. The system of claim 1, wherein the system includes two and only two ventricular struts.

12. The system of claim 1, wherein the central ring has a set fixed diameter when deployed, the diameter selected for a particular size of a tricuspid valve of the patient.

13. The system of claim 12, wherein the set diameter is any single diameter from within a range between 15 mm and 40 mm.

14. The system of claim 1, wherein the central ring is defined by a single wire.

15. The system of claim 14, wherein the wire has a gauge diameter between 0.2 mm and 0.8 mm.

16. The system of claim 14, wherein the wire extends along a circular shape to define the ring.

17. The system of claim 1, wherein each of the ventricular struts has a length that corresponds to a length of the ventricle and the atrial dome has a length that corresponds to a length of the atrium in a human heart.

18. The system of claim 1, wherein the system is configured and dimensioned such that the atrial dome and the ventricular struts stabilize the tricuspid valve replacement system within the heart in order for the valve to replace function of the native tricuspid valve without relying on an anchoring stent or barbs.

19. A method for tricuspid valve replacement, comprising:
placing a catheter containing the tricuspid valve replacement system of claim 1 in a collapsed state within a heart of a patient; and
removing the tricuspid valve replacement system from the catheter causing the tricuspid valve replacement device to transition from the collapsed state to an expanded state with the atrial dome positioned within a right atrium of the heart, the central ring and valve within an annulus of a native tricuspid valve of the heart, and the ventricular struts within a right ventricle of the heart so that the atrial dome and ventricular struts stabilize the tricuspid valve replacement system within the heart in order for the valve to replace function of the native tricuspid valve.

20. The method of claim 19, wherein the plurality of atrial struts comprise three atrial struts.

21. The method of claim 20, wherein the three atrial struts bow away from a central axis of the frame so that a maximum diameter of the atrial dome is larger than a maximum diameter of the central ring.

22. The method of claim 21, wherein the frame further comprises an end ring, and wherein the three atrial struts are coupled to and extend between the central ring and the end ring.

23. The method of claim 20, wherein the two ventricular struts each terminate at an atraumatic end with a curled end.

24. The method of claim 23, wherein the three atrial struts are uniformly positioned radially around the central ring,
wherein the two ventricular struts are positioned radially at opposite sides of the central ring, and
where the three atrial struts and two ventricular struts are positioned on the central in a non-overlapping manner.

25. The method of claim 19, wherein the catheter is 7 mm gauge or less.

26. The method of claim 25, wherein frame is formed of a shape memory alloy and self-expands from the collapsed state to the expanded state within the heart.

27. The method of claim 19, furthering comprising suturing the valve to the frame.

28. A method of manufacturing the tricuspid valve replacement system of claim 1, comprising:
providing the frame;
suturing the valve to the atrial dome of the frame; and
suturing the valve to the central ring of the frame.

* * * * *